United States Patent
Endo et al.

(10) Patent No.: US 8,542,271 B2
(45) Date of Patent: Sep. 24, 2013

(54) MONITOR DEVICE FOR USE WITH AN ENDOSCOPE APPARATUS

(75) Inventors: Takahisa Endo, Tachikawa (JP); Takemitsu Honda, Hachioji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 661 days.

(21) Appl. No.: 12/580,685

(22) Filed: Oct. 16, 2009

(65) Prior Publication Data

US 2010/0097453 A1 Apr. 22, 2010

(30) Foreign Application Priority Data

Oct. 17, 2008 (JP) ................................. 2008-268901

(51) Int. Cl.
*A62B 1/04* (2006.01)

(52) U.S. Cl.
USPC .............. 348/65; 348/70; 348/77; 348/268; 348/269; 348/270; 348/271; 348/560

(58) Field of Classification Search
USPC ............. 348/65, 70, 77, 268–269, 270–271, 348/560
See application file for complete search history.

(56) References Cited

U.S. PATENT DOCUMENTS

| 5,387,928 A * | 2/1995 | Nishimura ...................... 348/70 |
| 2005/0192476 A1* | 9/2005 | Homan et al. ................ 600/118 |
| 2007/0217765 A1* | 9/2007 | Itoh et al. ...................... 386/117 |
| 2008/0170116 A1* | 7/2008 | Nishibayashi et al. .... 348/14.02 |

FOREIGN PATENT DOCUMENTS

| JP | 60-48011 A | 3/1985 |
| JP | 2005-057588 A | 3/2005 |
| JP | 2007-068895 A | 3/2007 |

OTHER PUBLICATIONS

Japanese Office Action dated Feb. 12, 2013, issued in corresponding Japanese Patent Application No. 2008-268901 (English translation 14 pages).

* cited by examiner

*Primary Examiner* — Rupal Dharia
*Assistant Examiner* — Van Kim T Nguyen
(74) *Attorney, Agent, or Firm* — Westerman, Hattori, Daniels & Adrian, LLP (57) ABSTRACT

A monitor device for use with an endoscope apparatus, which has first and second display modes. In the first display mode, the monitor device displays, in real time, any image transmitted in a normal radio communication state. In the second display mode, the monitor device displays a noise-free image in real time, if a radio communication error occurs. If one-frame (or one-field) image data is not received within the frame (or field) time due to a communication error, the monitor device displays, in the second display mode, the image data received in a normal state immediately before the one-frame (or one-field) image data, and informs the operator of the communication error.

5 Claims, 8 Drawing Sheets

MONITOR DEVICE FOR USE WITH AN ENDOSCOPE APPARATUS

CROSS-REFERENCE TO RELATED APPLICATIONS

This application is based upon and claims the benefit of priority from prior Japanese Patent Application No. 2008-268901, filed Oct. 17, 2008, the entire contents of which are incorporated herein by reference.

BACKGROUND OF THE INVENTION

1. Field of the Invention

The present invention relates to a monitor device for use with an endoscope apparatus, which enables the operator of the endoscope apparatus to observe any image of an object, formed by an imaging device inserted in body cavities or ducts.

2. Description of the Related Art

In the field of medicine and the field of non-destruction inspection, endoscope apparatuses are usually used, each with a thin, long insertion section inserted into the body cavity or a duct, to monitor the image of an object existing in the body cavity or duct.

An endoscope apparatus of this type comprises an endoscope main unit, a light source device, a light guide cable, an imaging unit, a video processor, a signal cable, and a monitor device. The endoscope main unit has an insertion section that can be inserted into a body cavity or a duct. The light source device is provided outside the endoscope main unit and configured to apply light into the endoscope main unit. The light guide cable couples the light source unit to the endoscope main unit and can guide illumination light to the distal end of the endoscope main unit. The imaging unit is removably incorporated in the endoscope main unit and configured to photograph an object and generate an image signal representing the image of the object. The video processor converts the image signal generated in the endoscope main unit to an image signal representing an image that the monitor device can display. The signal cable can transmit the image signal to the video processor. The monitor device displays the image represented by the image signal.

Since the endoscope main unit is connected to the external devices by the light guide cable and the signal cable, its motion is limited by the length of these cables. Further, the operability of the endoscope main unit is somewhat limited by the weight and position of the cables.

In view of this, a new type of endoscope apparatus has been proposed. Jpn. Pat. Appln. KOKAI Publication No. 60-48011, for example, discloses an endoscope apparatus that incorporates an illumination device provided in the distal end and using light-emitting diodes (LEDs) as light source. This endoscope apparatus has no light guide cable, unlike the conventional apparatus that has a light guide cable extending from the proximal end of the endoscope main unit.

Electronic circuits have been miniaturized, thanks to the progress of one-chip fabrication and ultra-large-scale integration. At present, an endoscope apparatus is proposed, whose main unit incorporates both an image signal processing circuit and a transmitting circuit. The image signal processing circuit converts an image signal to a video signal that represents an image that can be displayed by a monitor device. The transmitting circuit transmits the video signal by radio. A receiving device, which is provided outside the endoscope apparatus, receives video signal from the transmitting circuit and demodulates the video signal. Thus, this endoscope apparatus does not have a signal cable, which may extends from the endoscope main unit.

Endoscope apparatuses of this type are called "wireless endoscopes," which can receive and transmit image data by radio. Having no data cables, the motion of their main unit is not so limited while the operator manipulates the endoscope main unit to observe the image of any object. In other words, the operability of the endoscope main unit is increased. As the operator moves the insertion section of the endoscope main unit is moved in a body cavity or a duct, the monitor device must display the image of the object in real time. To this end, the delay time between the generation of the image data and the display of the image data should be shortened as much as possible. In order to shorten delay time so much, the image data generated in the imaging unit of the endoscope apparatus is transmitted by radio in units of frames (or fields), each frame in frame time (or each field in field time), to the receiving unit of the receiving device. The receiving unit of the receiving device receives each frame within the frame time (or each field within the field time).

When the data is transmitted and received by radio, communication errors will be inevitably made due to the signal interference or reception failure induced by the environmental conditions.

Some methods that may be performed to prevent communication errors are known. One method is to transmit radio packets transmitted again and to add correction codes. This method can indeed lower the probability of communication errors, but cannot transmit all data in a normal sate within a specific time (one-frame time or one-field time) to shorten the delay time between the generation of the image data and the display of the image. Another method is to interpolate only packet data having an error in one frame, with the data corresponding to the frame received before in a normal state, or with the data of the packet being transmitted now.

BRIEF SUMMARY OF THE INVENTION

According to an embodiment of the present invention, there is provided a monitor device for use with an endoscope apparatus, comprising: receiving section to receive at least one from a still image and a moving image transmitted by radio from the endoscope apparatus; display section to display at least one from the still image and moving image received by receiving section; determining section to determine whether at least one from the still image and moving image has been received in a normal state; storage section to temporarily store at least one from the still image and moving image when the determining section determines that at least one from the still image and moving image has been received in a normal state; display control section to update at least one from the still image and moving image received in a normal state and causing the display section to display the still image and moving image updated, when the determining section determines that at least one from the still image and moving image has been received in a normal state, and for causing the display section to repeatedly display at least one from the still image and moving image temporarily stored, when the determining section does not determine that at least one from the still image and moving image has been received in a normal state; and notifying section to notify whether at least one from the still image and moving image displayed is an updated one or an image repeatedly displayed one.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of this invention will be described in detail, with reference to the accompanying drawings.

Figure 1:
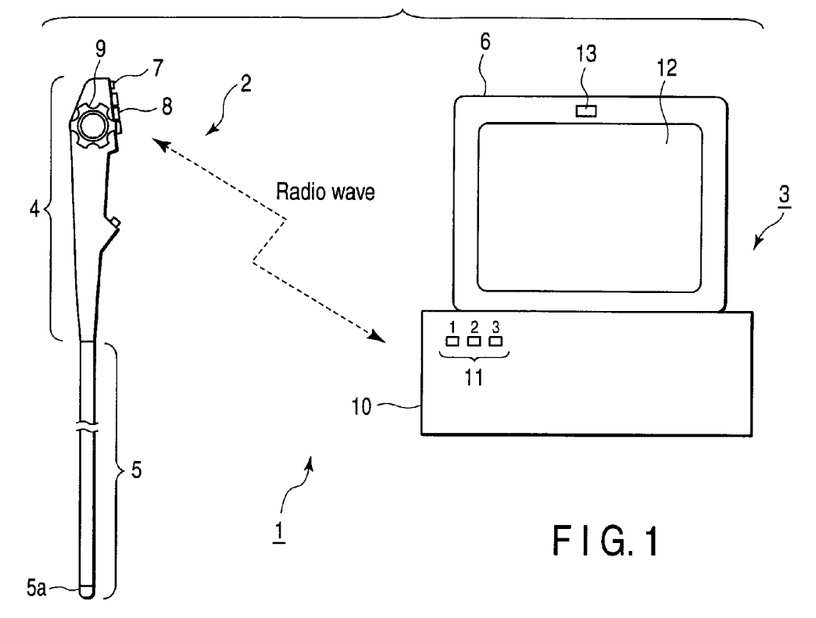
FIG. 1 is a diagram showing the outer appearance of an endoscope apparatus according to a first embodiment of this invention.
Figure 2:
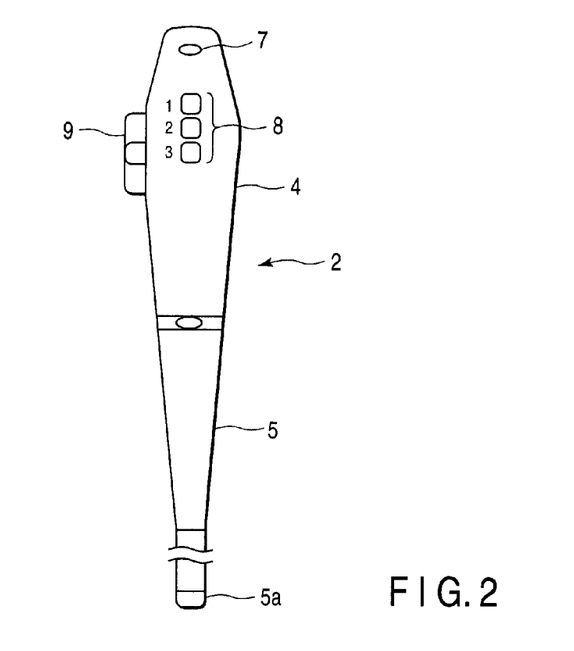
FIG. 2 is a diagram showing the outer appearance of the operation section of the endoscope main unit of the endoscope apparatus.
Figure 3:
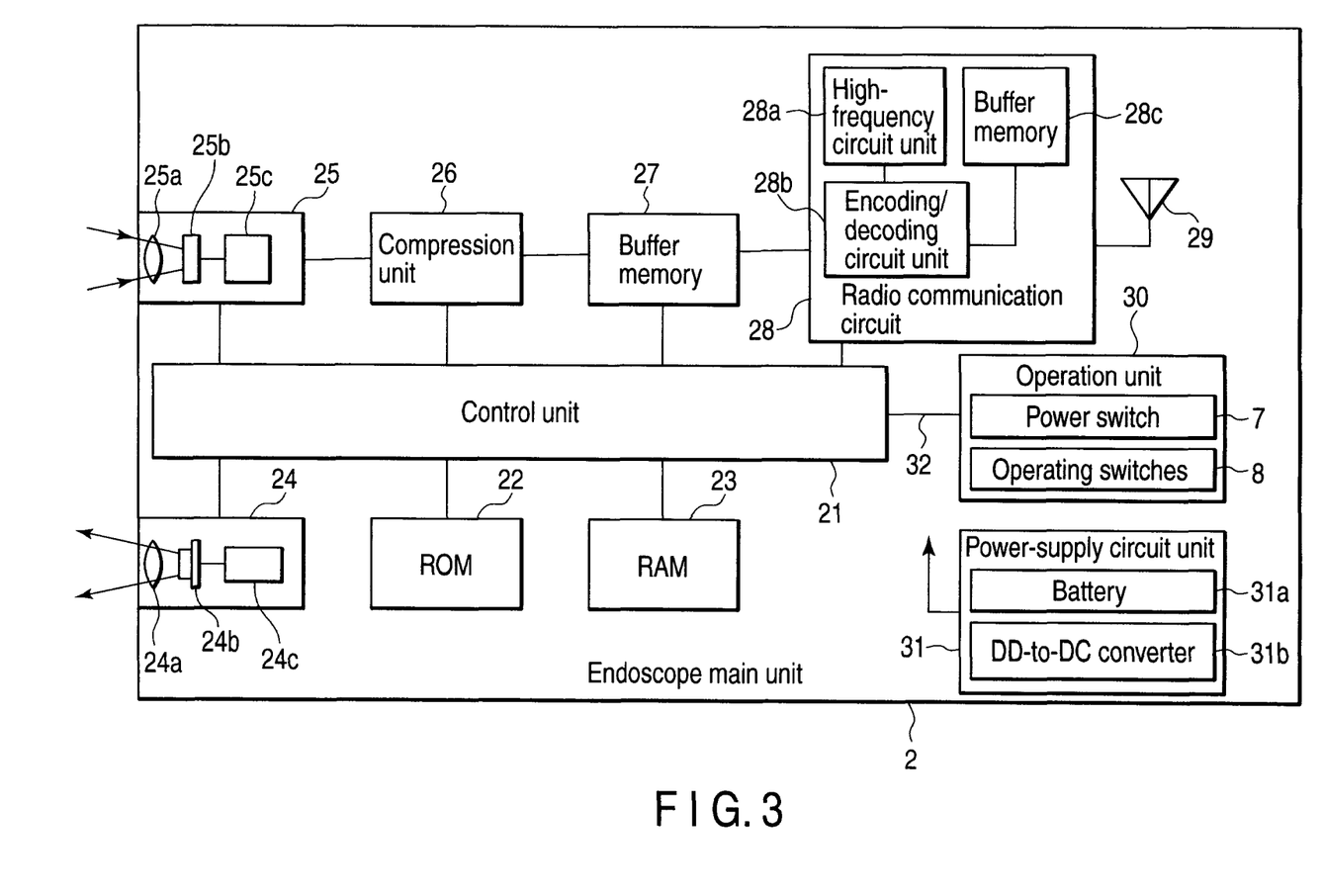
FIG. 3 is a block diagram showing the electrical configuration of the endoscope main unit.
Figure 4:
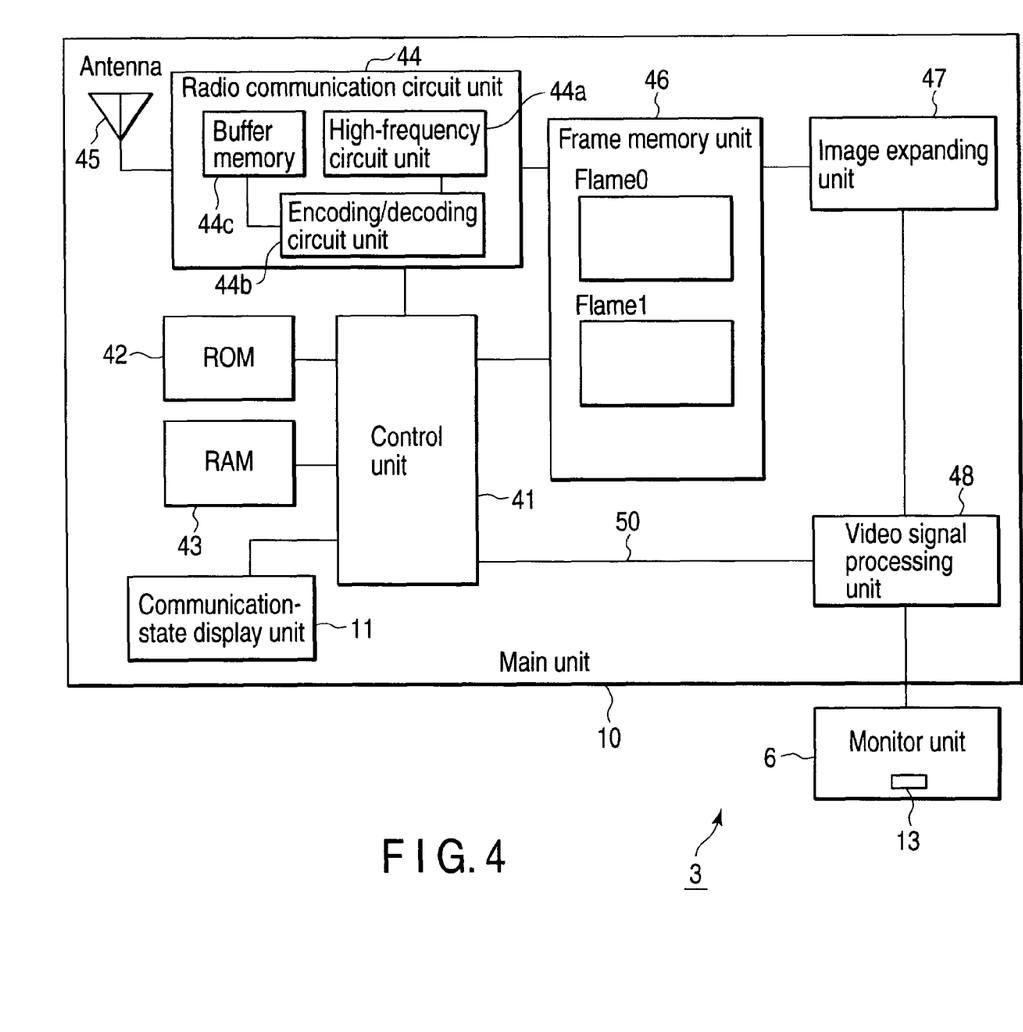
FIG. 4 is a block diagram showing the electrical configuration of the receiving device of the endoscope apparatus.

FIG. 1 shows the outer appearance of an endoscope apparatus according to a first embodiment of this invention. FIG. 2 shows the outer appearance of the operation section of the endoscope main unit of the endoscope apparatus. FIG. 3 is a block diagram showing the electrical configuration of the endoscope main unit (transmitting device). FIG. 4 is a block diagram showing the electrical configuration of the receiving device of the endoscope apparatus.

The endoscope apparatus 1 according to this embodiment comprises two major components, i.e., endoscope main unit 2 and receiving device 3. The endoscope main unit 2 transmits, by radio, the data representing a still or moving image photographed (hereinafter called "image data"). The receiving device 3 receives the image data transmitted by radio and supplies the same to a monitor unit 6. The monitor unit 6 displays at least one from the still image and the moving image represented by the image data.

The endoscope main unit 2 comprises an operation section 4 and a flexible insertion section 5. The distal end 5a of the insertion section 5 has windows for an imaging unit and an illumination unit, which will be described later. The distal end 5a may further have a forceps port.

As shown in FIG. 2, the operation section 4 has a power switch 7, a plurality of operating switches 8, and a dial switch 9. The operator may operate the operation switches 8 to input instructions for photographing an object and for observing the image of the object. The operator may operate the dial switch 9 to change the bending direction of the insertion section 5. The dial switch 9 may be replaced by a joystick-type switch. The operation switches 8 are assigned with serial numbers, e.g., 1, 2 and 3, and thereby distinguished from one another. The serial numbers may be replaced by symbol marks that represent the functions of the respective operation switches 8.

As shown in FIG. 1, the receiving device 3 comprises a monitor unit 6 and a main unit 10. The main unit 10 has a communication-state display unit 11.

The display unit 11 has a plurality of LEDs that can show the communication state. The monitor unit 6 has a display screen 12 and an error LED indicator 13, both arranged on the front. The error LED indicator 13 is located above the display screen 12. The LED indicator 13 emits green light, indicating that the monitor unit 6 is operating well, displaying a moving image. The LED indicator 13 may emit red light to indicate that the moving image is frozen due to an error. Any other display method can, of course, be used to inform the operator of an error.

The electrical configuration of the transmitting device of the endoscope main unit 2 will be described with reference to FIG. 3.

The endoscope main unit 2 comprises a control unit 21, a ROM 22, a RAM 23, an illumination unit 24, an imaging unit 25, an image compression unit 26, a buffer memory 27, a radio communication circuit 28, an antenna 29, an operation unit 30, and a power-supply circuit unit 31. A bus (wire) 32 connects these components to one another.

The components of the endoscope main unit 2 will be described below, in detail.

The power supply unit 31 supplies power to the other components of the endoscope main unit 2. The control unit 21 is constituted by a central processing unit (CPU). The CPU performs sequence control (or program control) on some of the other components of the endoscope main unit 2. The CPU performs other controls in accordance with the operator's instructions. The ROM 22 is a nonvolatile memory such as a flash ROM. The ROM 22 stores programs for driving the endoscope main unit 2 and various information items including communication-setting parameters. The control unit 21 performs controls in accordance with the preset conditions and programs, all stored in the ROM 22.

The RAM 23 is used as a work area when the control unit 21 performs operations, or as a storage area for temporarily hold various values set. Further, the RAM 23 may be used as an area for storing image compression parameters and communication-setting parameters.

The illumination unit 24 comprises an illumination lens 24a, a high-luminance LED 24b, and an LED drive circuit 24c. The high-luminance LED 24b emits a light beam. The light beam is applied, as illumination light, through the illumination lens 24a. The illumination lens 24a deflects and diverges the light beam, which illuminates an object existing in a body cavity. In this embodiment, a light source is arranged in the distal end 5a of the endoscope main unit 2. The configuration is not limited to this, nevertheless. The LED 24b may be arranged in the operation section 4. In this case, the illumination light emitted from the LED 24b is guided by a light guide (not shown) extending through the insertion section 5 and is applied through a window (not shown) made in the distal end 5a, illuminating the object existing in the body cavity.

The imaging unit 25 comprises a lens 25a, a photoelectric transducer 25b (CCD, MOS sensor, etc.), and an analog-to-digital converter 25c. The lens 25a focuses the incident light, forming an image. The photoelectric transducer 25b converts the image into an analog electrical signal. The analog-to-digital converter 25c digitizes the analog electrical signal.

The image compression unit 26 compresses the image data output from the imaging unit 25 and outputs the same to the buffer memory 27. The buffer memory 27 temporarily stores the image data output from the image compression unit 26. When the image data stored in the buffer memory 27 increases to a specific length, the data representing this fact is supplied to the control unit 21. On receiving this data, the control unit 21 supplies the compressed image data to the receiving device 3 through the radio communication circuit 28.

The radio communication circuit 28 comprises a high-frequency circuit unit 28a, an encoding/decoding circuit unit 28b, and a buffer memory 28c. The high-frequency circuit unit 28a and encoding/decoding circuit unit 28b are indispensable to radio communication. The radio communication circuit 28 is connected to the antenna 29.

This embodiment uses wireless LAN protocol 802.11 as a radio communication system. To accomplish radio communication with the receiving device 3, the endoscope main unit 2 must have the same channel (i.e., use frequency), the same SSID, etc., as the communication setting of the receiving device 3.

The operation unit 30 has at least a power switch 7 and operation switches 8. The operation unit 30 can assume various states when these switches are operated in various combinations. When the operation unit 30 assumes any state, it outputs an electrical signal that represents its state. The switches 8 serve as selection switches before the endoscope main unit 2 communicates by radio with the receiving device 3. Once radio communication has been established between the endoscope main unit 2 and the receiving device 3, the switches 8 can operated to freeze the moving image, save the still image and rotate the image during the medical operation.

The power supply unit 31 has at least a battery 31a and a DC-to-DC converter 31b. The battery 31a is, for example, a secondary battery. On detecting that the power switch 7 has been turned on, the power supply unit 31 supplies power to the other components of the endoscope main unit 2. The battery 31a may be a rechargeable one. In this case, it is removed from the endoscope main unit 2 and is then recharged with a recharger. Alternatively, the battery 31a may be one that can be recharged with radio waves, while remaining in the endoscope main unit 2. The endoscope main unit 2 may be driven with radio waves it receives so that its weight may be reduced. In this case, it should better be configured to keep operating for some time even after a communication error has occurred.

The configuration of the receiving device 3 will be described with reference to FIG. 4.

The receiving device 3 comprises a control unit 41, a ROM 42, a RAM 43, a radio communication circuit unit 44, an antenna 45, a frame memory unit 46, an image expanding unit 47, a video signal processing unit 48, and a monitor unit 6. A bus (wire) 50 connects these components to one another.

The control unit 41 comprises a central processing unit (CPU). The CPU processes image data and performs a sequence control (or program control) on the other components of the receiving device 3. Further, the CPU performs controls in accordance with the operator's instructions. The ROM 42 is a nonvolatile such as a flash ROM. The ROM 42 stores programs for driving the receiving device 3 and various setting information items. The control unit 41 performs a sequence control (or program control) on the receiving device 3 in accordance with the programs and preset conditions, all stored in the ROM 42.

The RAM 43 is used as a work area when the control unit 41 performs operations, or used as a storage area for temporarily hold various preset conditions. Further, the RAM 43 may be used as an area for storing image-expanding parameters and communication-setting parameters.

The radio communication circuit unit 44 comprises a high-frequency circuit unit 44a, an encoding/decoding circuit unit 44b, and a buffer memory 44c. The high-frequency circuit unit 44a and encoding/decoding circuit unit 44b are indispensable to radio communication. The radio communication circuit 44 is connected to the antenna 45. The radio communication circuit 44 performs radio communication in accordance with the wireless LAN protocol, as the radio communication circuit 28 does in the main unit 2.

The frame memory unit 46 is composed of two frame memories Frame 0 and Frame 1, each configured to store image data received. The image expanding unit 47 selects a memory area from which to read data, in accordance with the state of the register of the frame memory unit 46, Frame 1_Rdy or Frame 2_Rdy. The image expanding unit 47 then expands the compressed image data stored in the frame memory unit 46. The image data expanded is output to the video signal processing unit 48. The video signal processing unit 48 converts the image data to an NTSC signal or a PAL signal, which is output to the monitor unit 6. The monitor unit 6 comprises a display device and a control circuit for controlling the device. The display device is, for example, a liquid crystal panel.

Figure 5:
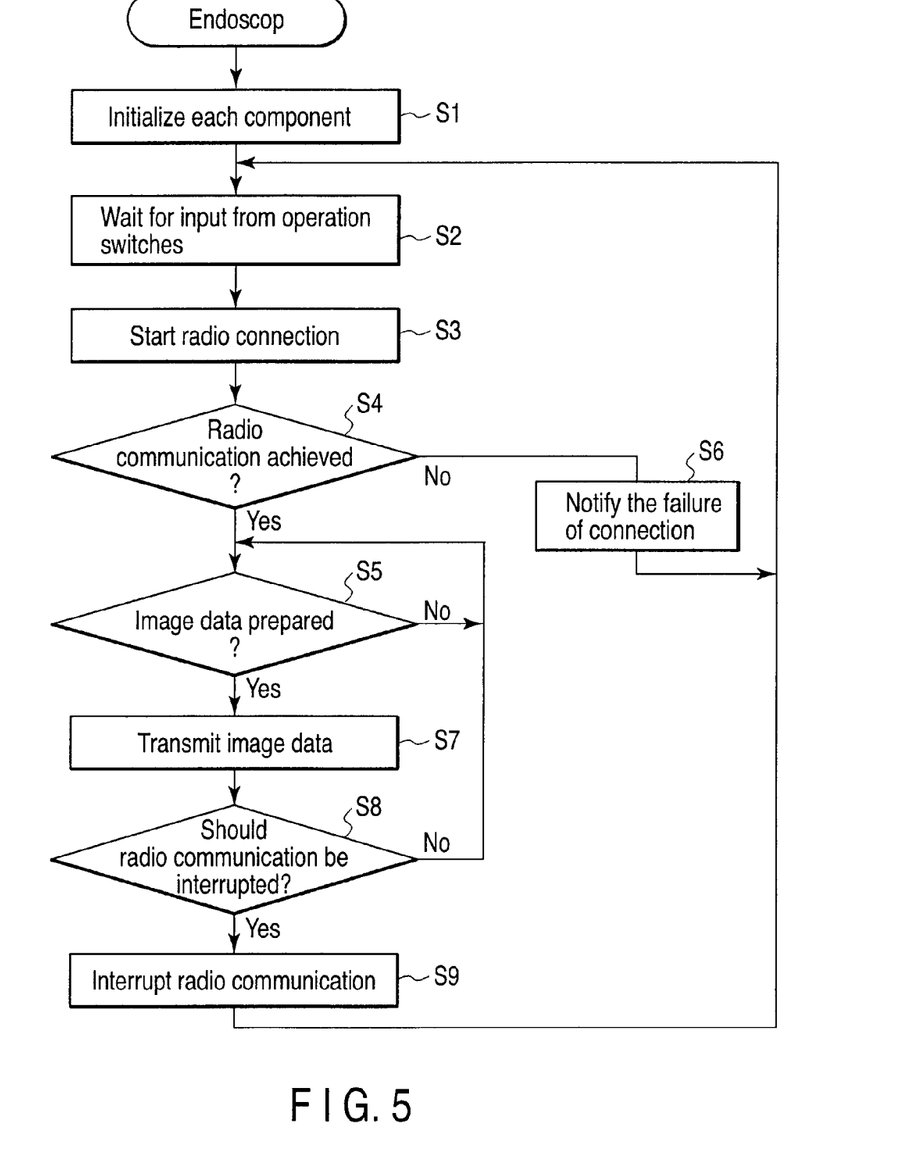
FIG. 5 is a flowchart explaining how the endoscope main unit operates to transmit data.

How the endoscope main unit 2 transmits the image data to the receiving device 3 will be explained, with reference to the flowchart of FIG. 5. In accordance with the operator's instructions, the control unit 21 controls the transmission sequence, transmitting the image data to the receiving device 3.

Assume that the operator turns on the power switch 7 of the endoscope main unit 2. Then, the control unit 21 initializes each component of the endoscope main unit 2 in accordance with a prescribed initialization sequence (Step S1). The control unit 21 starts waiting for inputs coming from the operation switches 8 (Step S2). The operator confirms the state of the communication-state display unit 11 and then operates one of the operation switches 8. The serial number assigned to the switch 8 operated is thereby input. The serial number input is stored in the RAM 43. The endoscope main unit 2 is connected by radio to the receiving device 3, in accordance with the radio connection parameter associated with the switch 8 operated (Step S3).

Next, the control unit 21 determines whether the endoscope main unit 2 has been connected by radio to the receiving device 3 (Step S4). If the endoscope main unit 2 has been connected to the receiving device 3 (YES in Step S4), the control unit 21 determines whether the image data has been stored into the buffer memory 27 (Step S5). If the endoscope main unit 2 has not been connected to the receiving device 3 (NO in Step S4), the control unit 21 generates an alarm, informing the operator of this fact (Step S6). Then, the control unit 21 returns to Step S2, in which it again starts waiting for inputs coming from the operation switches 8. The alarm may be an audio alarm generated by a sound source (not shown), such as a buzzer, provided in the endoscope main unit 2. Alternatively, the alarm may be a visual alarm displayed by the LED indicator 13.

If the control unit 21 finds that the image data has been stored into the buffer memory 27 (YES in Step S5), the image data is transmitted from the endoscope main unit 2 (Step S7). If the image data has not been stored into the buffer memory 27 (NO in Step S5), the control unit 21 repeats Step S5 until the image data is stored into the buffer memory 27. That is, the control unit 21 keeps monitoring the state of the buffer memory 27 (storing or not storing the image data). If the buffer memory 27 stores image data, the data will be transmitted to the receiving device 3, item by item. Each image data item thus transmitted contains ID data such as the frame number and intra-frame position number of the data item.

The control unit 21 determines whether the operator has operated an operation switch, instructing the interruption of the radio connection while the data is being transmitted to the receiving device 3 (Step S8). If the interruption of the radio connection has been instructed (YES in Step S8), the radio communication is interrupted (Step S9). In this case, the control unit 21 returns to Step S2, in which it again starts waiting for inputs coming from the operation switches 8. If any operation switch is operated in this state, the endoscope main unit 2 is again connected to the receiving device 3 in accordance with the communication parameter associated with the serial number of the operation switch 8 operated. If the interruption of the radio connection has not been instructed (NO in Step S8), the transmission of the image data is continued.

Figure 6:
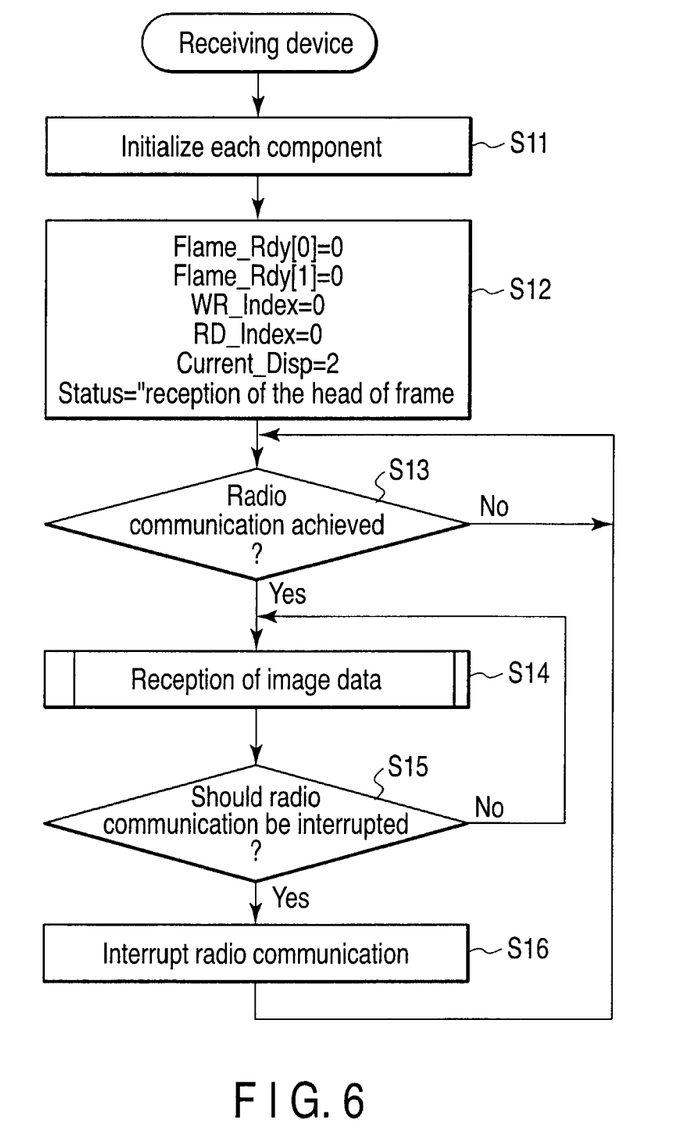
FIG. 6 is a flowchart explaining how the receiving device operates to receive data in the endoscope apparatus.

How the receiving device 3 receives data from the endoscope main unit 2 will be explained, with reference to the flowchart of FIG. 6. In the receiving device 3, the control unit 41 controls the data-receiving sequence, determining whether the image data has been received in a normal state.

When the power switch (not shown) of the receiving device 3 is turned on, the other components of the receiving device 3 are activated. The control unit 41 initializes each component of the receiving device 3 in accordance with the prescribed initialization sequence and accomplishes an appropriate communication setting in accordance with the radio environment of the receiving device 3 (Step S11). Alternatively, when the power switch 7 of the endoscope main unit 2 may be turned on, activating the other components of the endoscope main unit 2. In this case, the operator may input an instruction from the endoscope main unit 2, thereby activating the receiving device 3.

The control unit 41 initializes the parameters that control the frame memory unit 46, as shown below (Step S12).

Frame_Rdy[0]=0
Frame_Rdy[1]=0
WR_Index=0
RD_Index=0
Current_Disp=2
Status="Reception of the head of frame"

Frame_Rdy[0] is a parameter that indicates that the image data that Frame 0 receives has been stored in a normal state in the frame memory unit 46. Frame_Rdy[1] is a parameter that indicates that the image data that Frame 1 receives has been stored in a normal state in the frame memory unit 46. WR_Index indicates the frame memory that stores the received data. RD_Index indicates the frame memory from which the data is output to the image expanding unit 47. Current_Disp indicates the frame memory storing the data being displayed at present. Thus, WR_Index, RD_Index and Current_Disp designate "Frame 0" if they are all "0," and designates "Frame 1" if they are all "1." Next, the control unit 41 receives a connection instruction from the endoscope main unit 2 and determines whether the radio connection has been established (Step S13). If the radio connection has been established (YES in Step S13), the receiving device 3 starts receiving the image data from the endoscope main unit 2 (Step S14). If the radio connection has not been established (NO in Step S13), the receiving device 3 waits for the image data. The image data received is displayed by the monitor unit 6.

Then, the control unit 41 determines whether the operator has operated an operation switch, instructing that the radio connection be interrupted (Step S15). If the interruption of radio connection has been instructed (YES in Step S15), the radio connection is interrupted (Step S16). After the radio connection has been interrupted, the control unit 41 returns to Step S13, whereby the receiving device 3 assumes the initial state and starts waiting for the next instruction for radio connection. On receiving the next instruction, the receiving device 3 is connected by radio to the endoscope main unit 2.

If the interruption of radio connection has not been instructed (NO in Step S15), the receiving device 3 keeps receiving the image data from the endoscope main unit 2.

Figure 7A:
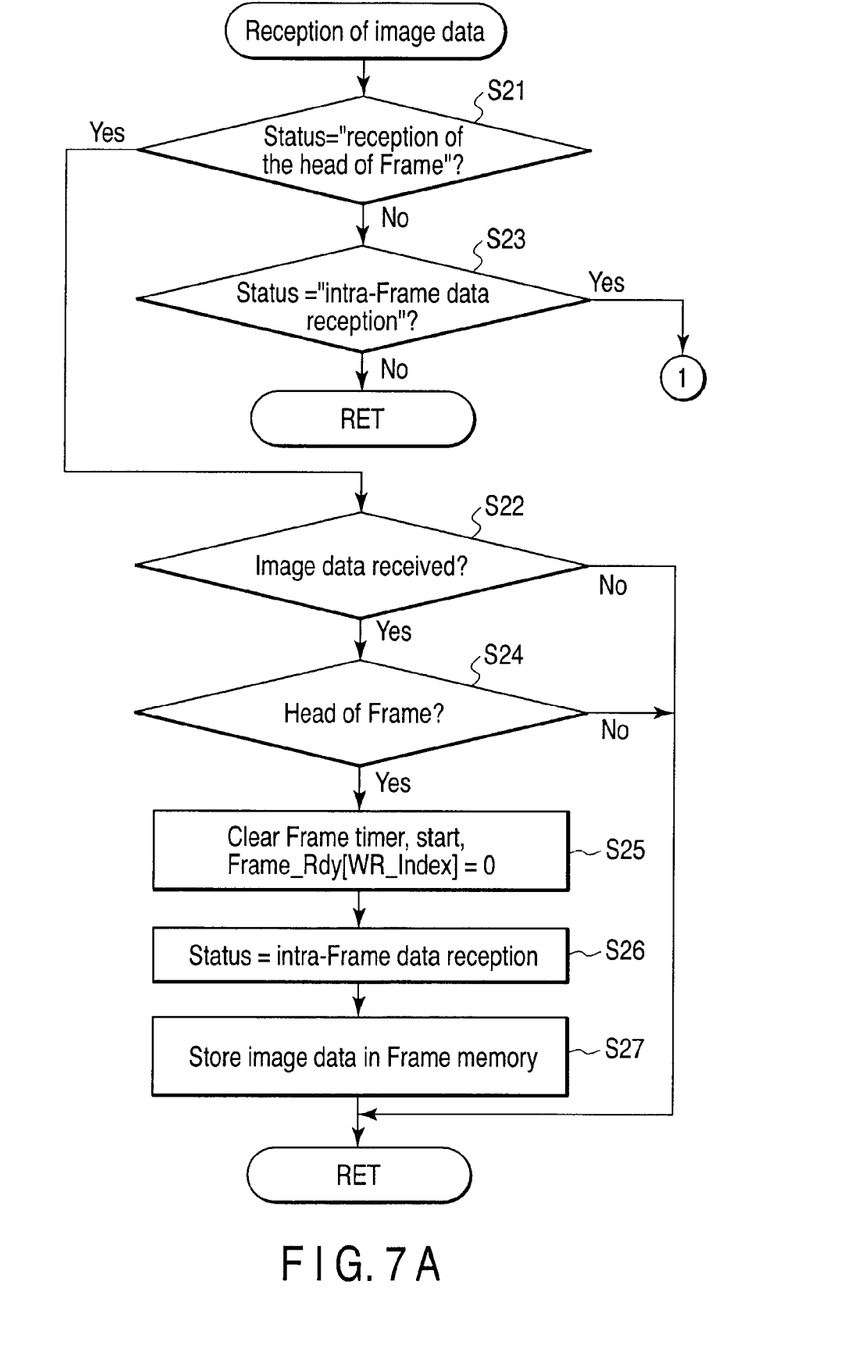
FIG. 7A is a flowchart explaining how image data is received in Step 14 shown in FIG. 6.
Figure 7B:
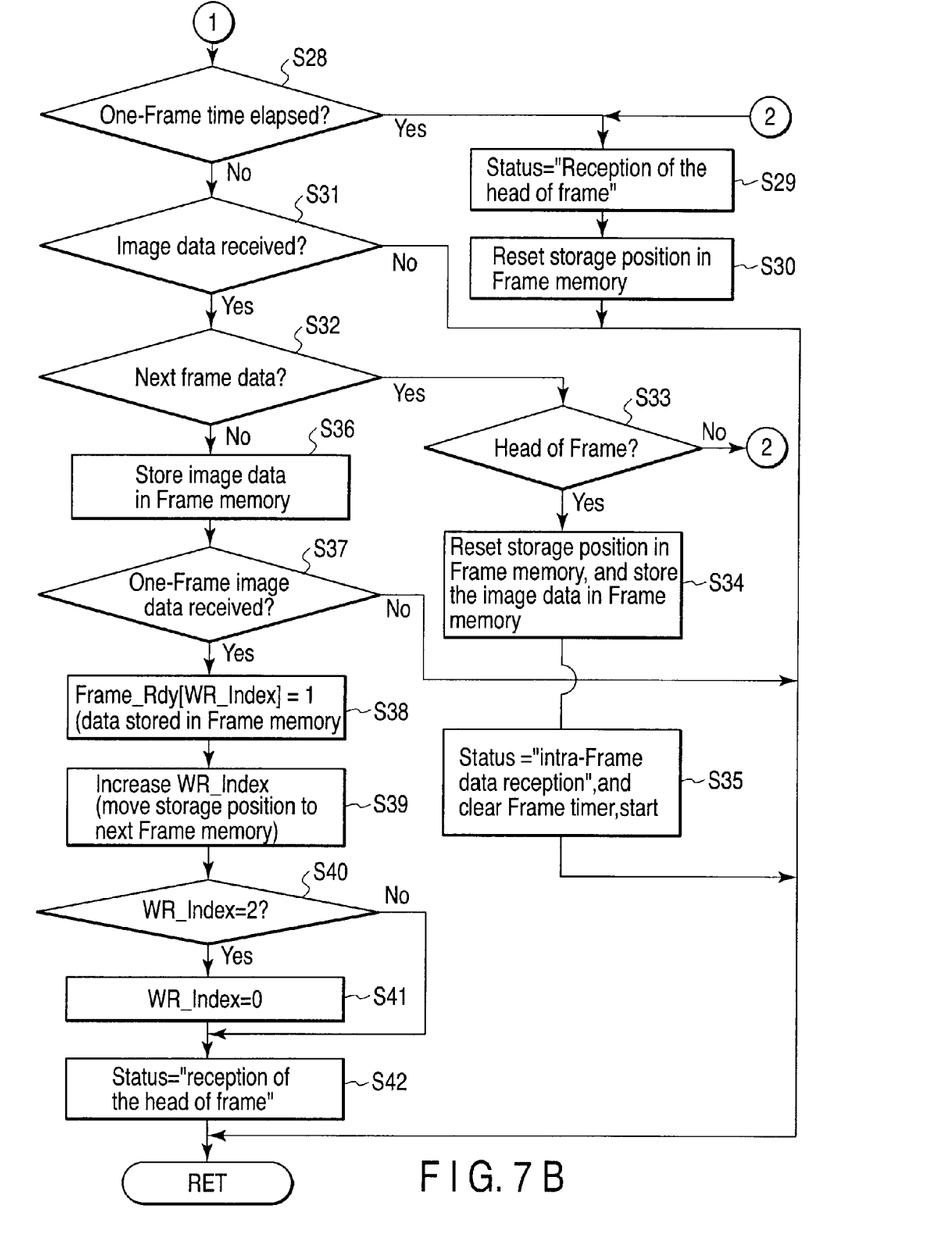
FIG. 7B is a flowchart explaining how the image data is received in steps following Step 23 shown in FIG. 7A.

How the receiving device 3 receives the image data in Step S14 will be explained, with reference to the flowchart (subroutine) of FIGS. 7A and 7B.

First, the control unit 41 determines whether "Reception of the head of frame" has been set in Status (Step S21). Note that "Status" is data that represents how the receiving device 3 is operating while receiving the image data from the endoscope main unit 2. If Status is "Reception of the head of frame," it indicates that the head of the frame, i.e., the start of reception of the frame, is being searched for. If "Reception of the head of frame" has been set in Status (YES in Step S21), the control unit 41 determines whether the image data has been received (Step S22). If "Reception of the head of frame" has not been set in Status (NO in Step S21), the control unit 41 determines whether "Intra-frame data reception" has been set in Status (Step S23). If Status is "Intra-frame data reception," it shows that the head of frame has been received and that the image data remaining in the next frame is being received.

If "Intra-frame data reception" is not set in Status (NO in Step S23), the control unit 41 returns to Step S15 (FIG. 6), which will be described later. If "Intra-frame data reception" is set in Status (YES in Step S23), the control unit 41 goes to Step S28, which will be described later.

If the image data has been received (YES in Step S22), the control unit 41 determines whether the image data is the head of the frame (Step S24). If the image data has not been received (NO in Step S22), the control unit 41 returns to Step S15.

If the image data is not the head of the frame (NO in Step S24), the control unit 41 returns to Step S15, too. If the image data is the head of the frame (YES in Step S24), the count of the frame timer incorporated in the control unit 41 is cleared, and the frame timer starts measuring time (Step S25). At this point, the Frame_Rdy[WR_INDEX] is set to "0."

Next, "Intra-frame data reception" is set in Status (Step S26). Then, the image data is stored into the frame memory unit 46 (Step S27), and the control unit 41 returns to Step S15.

"Intra-frame data reception" may be found set in Status (that is, YES in Step S23). In this case, the control unit 41 determines whether the time required to receive one frame (i.e., one-frame time) has elapsed after the receipt of the image data (Step S28). If the one-frame time has elapsed (YES in Step S28), "Reception of the head of frame" is set to Status (Step S29). The storage position of the image data is then reset to the head address of the frame memory that stores the image data (Step S30). Then, the control unit 41 returns to Step S15.

Hence, the frame memory unit 46 is not switched if one frame of image data is not received within the preset time (i.e., one-frame time) due to a communication error. Instead, preparation is made to store the next frame data to come. Therefore, the other frame memory holds the frame preceding the present frame.

If the count of the frame timer has not reached the time required to receive one frame (i.e., one-frame time), after the receipt of the image data (NO in Step S28), the control unit 41 again determines whether the image data has been received (Step S31). If the image data has not been received (NO in Step S31), the control unit 41 returns to Step S15, too. If the image data has been received (YES in Step S31), the control unit 41 determines whether the image data pertains to the next frame (Step S32).

If the image data pertains to the next frame (YES in Step S32), the control unit 41 determines whether this image data pertains to the head of frame (Step S33). If the image data pertains to the head of frame (YES in Step S33), the control unit 41 resets the image data at the head address of the frame memory (Step S34) and set "Intra-frame data reception" in Status, after the count of the frame timer incorporated is cleared, and the frame timer starts measuring time (Step S35). The control unit 41 then returns to Step S15. If the image data dose not pertain to the next frame (NO in Step S32), the control unit 41 stores the image data in the frame memory (Step S36).

Next, the control unit 41 determines whether the image data stored in a normal state pertains to one frame (Step S37). If one-frame image data has been received in a normal state (YES in Step S37), the frame memory of the frame memory unit 46 is switched to the next frame memory. That is, "1" is set for Frame Rdy [WR_Index] (Step S38). This shows that the data has been completely stored into the frame memory. Then, the control unit 41 increases WR_Index by one (Step S39). This changes the storage position of the image data to the next frame memory.

The control unit 41 then determines whether WR_Index has increased to 2 (Step S40). If WR_Index has increased to 2 (YES in Step S40), the control unit 41 resets WR_Index back to 0 (Step S41), and changes Status to "Reception of the head of frame" (Step S42). As a result, the image data received next is stored into the next frame memory. If WR_Index has not increased to 2 (NO in Step S40), the control unit 41 goes to Step S41, in which Status is changed to "Reception of the head of frame."

If one-frame image data has been received in a normal state (NO in Step S37), the control unit 41 returns to Step S15, whereby the reception of image data is continued.

How the receiving device 3 displays the image data will be explained, with reference to the flowchart (subroutine) of FIG. 8.

Figure 8:
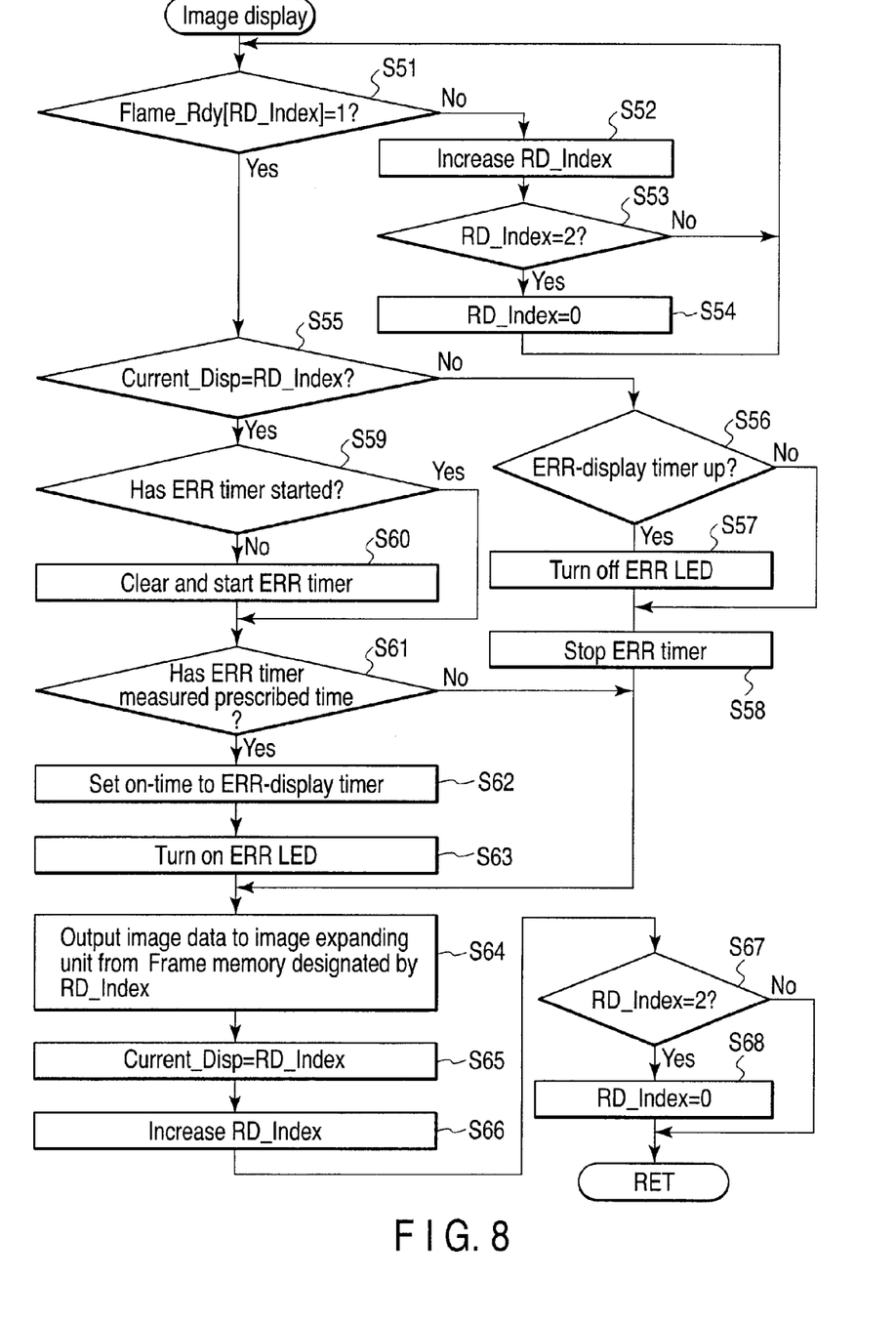
FIG. 8 is a flowchart explaining, in detail, how the receiving device operates to display the image data.

Every time the image expanding unit 47 issues a request for data, the subroutine of FIG. 8 is performed to make the monitor unit 6 display an image. The control unit 41 determines whether the image data has been received in a normal state and then causes the monitor unit 6 to display the image data.

First, the control unit 41 discriminates Frame_Rdy [RD_Index] that indicates the state the image data assumes in each frame memory. Any frame memory that stores image data in a normal state is thereby selected. In other words, the control unit 41 determines whether "1" is set for Frame_Rdy [RD_Index] (Step S51). If "1" is not set to Frame_Rdy [RD_Index] (NO in Step S51), RD_Index is increased by one (Step S52). After RD_Index has been so increased, the control unit 41 determines whether RD_Index has changed to "2" (Step S53). If RD_Index has not changed to "2" (NO in Step S53), the control unit 41 returns to Step S51. If RD_Index has changed to "2" (YES in Step S53), the control unit 41 changes the index to "0" (Step S54).

If "1" is set for Frame_Rdy[RD_Index] (YES in Step S51), the control unit 41 determines whether RD_Index is identical to Current_Disp (Step S55). That is, control unit 41 determines whether the frame memory from which the image data now being displayed has been read is the very frame memory from which to output the image data to the image expanding unit 47. If RD_Index is identical to Current_Disp (YES in Step S55), it shows that a communication error has occurred. In other words, the control unit 41 determines that the image data is being received in a normal state if RD_Index is not identical to Current_Disp (NO in Step S55), or if the frame memory is not identical to that frame memory. Next, the control unit 41 determines whether the error-displaying timer incorporated in it has "time-up state" (Step S56). If the error-displaying timer has "time-up state" (YES in Step S56), the control unit 41 turns off the LED indicator 13 (Step S57), and the ERR timer has stopped measuring time (Step S58).

In this case, the control unit 41 reads the image data from the frame memory selected and outputs the same to the image expanding unit 47. The image expanding unit 47 expands the image data. The image data expanded is input to the video signal processing unit 48. The video signal processing unit 48 converts the image data to an NTSC signal or a PAL signal, which is output to the monitor unit 6. The monitor unit 6 displays, in the first display mode, the image represented by the NTSC or PAL signal (Step S64). If the error-displaying timer does not have "time-up state" (NO in Step S56), the control unit 41 goes to Step S58.

In Step S55, RD_Index may be found identical to Current_Disp, or the frame memory may be found identical to that frame memory. In this case, the control unit 41 determines that a communication error has occurred and that no new image data has been received. The display mode is therefore switched to the second display mode. Then, the control unit 41 determines whether the ERR timer has started measuring time (Step S59). If the ERR timer has not started (NO in Step S59), the control unit 41 clears the ERR timer and makes the ERR timer starts measuring time again (Step S60). If the ERR timer has started measuring time (YES in Step S59), the control unit 41 makes the ERR timer keep measuring time.

If the frame memory storing the image data representing the image being displayed is identical to the frame memory selected, the control unit 41 determines whether the time the ERR timer has measured exceeds a preset time (Step S61). (The preset is the time the operator needs to recognize that the moving image is frozen, for example time equivalent to several frames, which depends on the characteristic of the image.) If the time exceeds the preset time (YES in Step S61), the control unit 41 determines that a communication error has occurred.

The image data not updated yet is displayed at this point. The control unit 41 therefore sets to the error-displaying timer a prescribed time for which to inform the operator that the moving image is frozen (Step S62). Then, the timer starts measuring time, and the LED indicator 13 is turned on (Step S63).

Next, the image data is supplied from the frame memory designated by RD_Index, i.e., frame memory selected at present, to the monitor unit 6, which displays the image data (Step S64). Thereafter, Current_Disp is updated to RD_Index (Step S65). RD_Index is increased by one (Step S66). After RD_Index has been so increased, the control unit 41 determines whether RD_Index has changed to "2" (Step S67). If RD_Index has not changed to "2" (NO in Step S67), the control unit 41 then returns to Step S15. If RD_Index has changed to "2" (YES in Step S67), the control unit 41 changes the index to "0" (Step S68). The control unit 41 then returns to Step S15.

In the present embodiment, an LED emits light, informing the operator of any communication error that has occurred. Further, a notice of the communication error may be displayed on the screen of the monitor unit 6, along with the image being displayed on the screen. Moreover, the image data may be controlled not only in units of frames, but also in units of fields. Furthermore, the image displayed in place of an erroneous image may be not only a moving image, but also a still image.

As described above, the receiving device of the endoscope apparatus according to this embodiment has two display modes. In the first display mode, the device displays the image received in normal radio communication, in real time. In the second display mode, the device displays the image in real time, as an image free of noise, if an error has occurred in the radio communication. In the second display mode, any image data for one frame (one field), not received in a normal state within a prescribed frame time (or field time) due to a communication error, is replaced by the image data received in a normal state for the immediately preceding frame. As a result, an image free of noise can be displayed, while achieving real-time display, even if an error occurred in the radio communication.

In the second display mode, too, the operator can be informed of the fact that the moving picture is not being displayed in a normal state due to a communication error, if the image data remains not updated for a prescribed time or a longer time due to the communication error. So informed, the operator knows that any image that moves too slowly, does not move at all or is repeatedly displayed is an erroneous one. This enables the operator to make correct diagnosis, ultimately avoiding risks. A surgeon, for example, can know that a communication error is occurring, while performing surgery on an object in a body cavity, by using an endoscope. He or she can therefore perform the surgery safely.

The endoscope main unit 2 and the receiving device 3 need not be connected with cables, because the image data is exchanged between them by radio communication. That is, they are separated from each other. This increases the operability of the endoscope main unit 2, enables the operator to position the insertion section 5 at various angles in the body cavity, ultimately reducing the fatigue on the part of the operator. This also increases the freedom of positioning the endoscope main unit and receiving device, enabling the operator to arrange the monitor unit so that he or she may observe the image most easily.

An endoscope apparatus designed to detect cracks or holes made in a duct is used displays similar images one after another as the interior of the duct is photographed. Inevitably, the operator may fail to notice a communication error, if any, for some time. If this invention is applied to such an endoscope apparatus, a communication error can be detected when the receiving device fails to receive the image data representing the image photographed, no matter whether the images photographed are similar or not. Upon noticing a communication error, the operator stops operating the apparatus. When the communication is resumed, the operator may operate the apparatus again.

The embodiment described above includes the following inventions:

(1) A monitor device for use in an endoscope apparatus that comprises an endoscope configured to transmit, by radio communication, image data in units of frames (or fields), each within frame time (or field time), and a receiving device having a receiving unit configured to receive the image data transmitted from the endoscope and an image display unit configured to display the image data received by the receiving unit at the frame time (or field time). The monitor device has a second display mode. If one-frame (or one-field) image data is not received within the frame (or field) time, the one-frame image data received before in a normal state is displayed instead, in the second display mode.

The monitor device of the endoscope apparatus has the second display mode. If one-frame (or one-field) image data is not received within the frame (or field) time, the one-frame image data received in a normal state before is displayed instead, in the second display mode. An image free of noise can therefore be displayed in real time, even if a radio communication error occurs.

(2) A monitor device for use with an endoscope apparatus, which has a second display mode. In the second display mode, the monitor device displays image data, while informing the operator that the moving picture is not being displayed in a normal state due to a communication error, if the image data remains not updated, in the first display mode, for a prescribed time or a longer time due to the communication error.

This monitor device of the endoscope apparatus displays image data, while informing the operator that the moving picture is not being displayed in a normal state due to a communication error, if the image data remains not updated, in the second display mode, for a prescribed time or a longer time due to the communication error. The user can therefore easily recognize whether the image changes or not, even in a scene consisting of similar images displayed one after another.

The monitor device of the endoscope apparatus, according to the embodiment described above, updates, in real time, the image data transmitted in a normal radio communication state and displays the image data updated. If one-frame (or one-field) image data is not received within the frame (or field) time, the one-frame image data received in a normal state before is repeatedly displayed in place of the one-frame (or one-field) image data not received in a normal state.

The monitor device of the endoscope apparatus can therefore display a noise-free image even if a radio communication error occurs while the image photographed is being displayed in real time.

What is claimed is:

1. A monitor device for use with an endoscope apparatus, comprising:
    a radio receiving section to receive image data transmitted by radio successively from the endoscope apparatus;
    a display section to display the image data received by radio receiving section;
    a determining section to determine whether the image data started to be received by radio by the radio receiving section has been received by radio in a normal state within a predetermined period;
    a storage section to temporarily store the image data which has been received by radio in the normal state when the determining section determines that the image data has been received in the normal state;
    a display control section to update the image data received by radio in the normal state and causing the display section to display the image data updated, when the determining section determines that the image data has been received by radio in the normal state, and for causing the display section to repeatedly display the image data temporarily stored, when the determining section does not determine that the image data has been received by radio in the normal state; and
    an informing section to inform an operator whether the image data displayed in the display section is the updated image data or the repeatedly displayed image data, wherein
    the determining section determines that the image data assumes the normal state when the image data is received by radio before a predetermined time expires and
    the determining section determines whether the image data has been received by radio in the normal state, repeatedly at intervals of a prescribed time.

2. The monitor device for use with an endoscope apparatus, according to claim 1, wherein the predetermined time is equal to or shorter than at least one-frame or one-field time of a moving image of the image data.

3. The monitor device for use with an endoscope apparatus, according to claim 1, wherein the prescribed time is equal to or shorter than at least one-frame or one-field time of a moving image of the image data.

4. The monitor device for use with an endoscope apparatus, according to claim 1, wherein the display section also serves as the informing section by displaying information to show that repetitive display is carried out.

5. A method for displaying image data of monitor device for use with an endoscope apparatus, the method comprising the steps of:

receiving the image data by radio successively from the endoscope apparatus;

determining whether the image data started to be received by radio has been received by radio in a normal state within a predetermined period;

temporarily storing the image data which has been received by radio in the normal state when it is determined that the image data has been received in the normal state by the determining;

display controlling to update and display the image data received by radio in the normal state when it is determined that the image data has been received by radio in the normal state by the determining, and to repeatedly display the image data temporarily stored when it is determined that the image data has not been received by radio in the normal state by the determining; and informing an operator whether the image data displayed is the updated image data or the repeatedly displayed image data, wherein the determining determines that the image data assumes the normal state when the image data is received by radio before a predetermined time expires; and the determining determines whether the image data has been received by radio in the normal state, repeatedly at intervals of a prescribed time.

* * * * *